(12) United States Patent
Yeole et al.

(10) Patent No.: US 10,017,797 B2
(45) Date of Patent: Jul. 10, 2018

(54) CONTINUOUS BIOTRANSFORMATION OF SUBSTITUTED AROMATIC CARBOXYLIC ACIDS TO THEIR SELECTIVE ALDEHYDES AND ALCOHOLS

(71) Applicant: PRIVI BIOTECHNOLOGIES PRIVATE LIMITED, Mumbai, Maharashtra (IN)

(72) Inventors: Mahendra M Yeole, Mumbai (IN); Arvind M. Lali, Mumbai (IN)

(73) Assignee: PRIVI BIOTECHNOLOGIES PRIVATE LIMITED, Navi Mumbai, Maharashtra (IN)

(*) Notice: Subject to any disclaimer, the term of this patent is extended or adjusted under 35 U.S.C. 154(b) by 254 days.

(21) Appl. No.: 14/424,653

(22) PCT Filed: Aug. 28, 2013

(86) PCT No.: PCT/IN2013/000526
§ 371 (c)(1),
(2) Date: Feb. 27, 2015

(87) PCT Pub. No.: WO2014/045299
PCT Pub. Date: Mar. 27, 2014

(65) Prior Publication Data
US 2015/0252397 A1 Sep. 10, 2015

(30) Foreign Application Priority Data
Aug. 28, 2012 (IN) .................. 2497/MUM/2012

(51) Int. Cl.
*C12P 1/00* (2006.01)
*C12P 1/04* (2006.01)
(Continued)

(52) U.S. Cl.
CPC ............... *C12P 13/001* (2013.01); *C12P 7/22* (2013.01); *C12P 7/24* (2013.01); *C12R 1/645* (2013.01); *Y02P 20/582* (2015.11)

(58) Field of Classification Search
None
See application file for complete search history.

(56) References Cited

U.S. PATENT DOCUMENTS 5,262,315 A * 11/1993 Gross ..................... C12P 7/24
                                                                435/147
5,866,380 A *  2/1999 Lesage-Meessen ...... C12P 7/24
                                                                435/146
(Continued)

OTHER PUBLICATIONS

C. Stentelaire et al., "Short Communication: By-passing of unwanted vanillyl alcohol formation using selective adsorbents to improve vanillin production with Phanerochaete chrysosporium," World Journal of Microbiology & Biotechnology, vol. 14, pp. 285-287, 1998.

(Continued)

*Primary Examiner* — Chris R Tate
*Assistant Examiner* — Douglas F White
(74) *Attorney, Agent, or Firm* — Drinker Biddle & Reath LLP

(57) ABSTRACT

The present invention discloses a novel method for biological reduction of the carboxylic acids to their corresponding aldehydes and/or alcohols with high productivity and high yield by using fungus in the category of basidiomycetes. This reduction is specific and selective for its functional group (—COOH), without affecting other functional group such as—R groups (—OH, —NH2, -alkyl, -alkyoxy) and their position, number on aromatic ring. The method of the invention relates to reduction of aryl acids to aldehyde and/or alcohols by employing a white rot fungus—*Pycnoporus cinnabarinus*, an organism of basidiomycete species, (Continued)

grown in vessel/column. The biotransformation was performed in vessel/column/fermentor with pH control, dissolved oxygen, membrane system, product extractor is attached.

21 Claims, 2 Drawing Sheets

(51) Int. Cl.

| | | |
|---|---|---|
| C12P 13/00 | (2006.01) | |
| C12P 7/22 | (2006.01) | |
| C12P 7/24 | (2006.01) | |
| C12R 1/645 | (2006.01) | |

(56) References Cited

U.S. PATENT DOCUMENTS

| | | |
|---|---|---|
| 6,162,637 A | 12/2000 | Lesage-Meessen et al. |
| 6,372,461 B1 * | 4/2002 | Frost .................. C12N 9/0008 435/156 |
| 2006/0292676 A1 * | 12/2006 | Sun .......................... C12P 7/42 435/136 |
| 2008/0060257 A1 * | 3/2008 | Duyvesteyn ............. C09K 8/58 44/300 |
| 2011/0297172 A1 * | 12/2011 | Lalleman ............... A61Q 5/065 132/208 |

OTHER PUBLICATIONS

C. Stentelaire et al., "Design of a Fungal Bioprocess for Vanillin Production from Vanillic Acid at Scalable Level by Pycnoporus cinnabarinus," Journal of Bioscience and Bioengineering, vol. 89, No. 3, pp. 223-230, 2000.

L. Lesage-Meesen et al., "A two-step bioconversion process for vanillin production from ferulic acid combining Aspergillus niger and Pycnoporus cinnabarinus," Journal of Biotechnology, vol. 50, pp. 107- 113, 1996.

* cited by examiner

CONTINUOUS BIOTRANSFORMATION OF SUBSTITUTED AROMATIC CARBOXYLIC ACIDS TO THEIR SELECTIVE ALDEHYDES AND ALCOHOLS

FIELD OF INVENTION

The present invention discloses a novel method for biological reduction of the carboxylic acids to their corresponding aldehydes and/or alcohols with high productivity and high yield by using fungus in the category of basidiomycetes. This reduction is specific and selective for its functional group (—COOH), without affecting other functional group such as—R groups (—OH, —NH2, -alkyl, -alkyoxy) and their position, number on aromatic ring.

BACKGROUND OF THE INVENTION

With the improvement of living conditions, consumers' desire for healthy and green products from natural origin has increased and thus has accelerated the launch activity for products of natural origin. In contrast to chemical synthesis, biological synthesis has the advantages of mild reaction condition, fewer byproducts, lesser environmental pollution, selectivity and simple downstream processing. Hence research directed towards the microbial biosynthetic pathway to produce natural flavor, food stabilizer etc is gaining significance. Natural aromatic compounds including benzaldehyde, vanillin, p-hydroxy benzoic acid are already in demand and represent a very large market size in the flavor and food industry.

Aromatic, aliphatic and alicyclic aldehydes and alcohol are useful intermediates in the chemical, pharmaceutical, food and flavor industries. Chemical methods for conversion of carboxylic acids to aldehyde or alcohol are limited and they usually require prior derivatization (esterification) and product de-blocking with reactants containing competing functional group (JP2010227893A).

An efficient route to synthesize aryl aldehydes and alcohols from aryl acids is to use the reductive enzyme system of white rot Basidiomycetes as biocatalyst. The white rot fungi with reducing activities include *Trametes versicolor* (Farmer et al., *Biochim. Biophys. Acta.* 35 (1959) 202-211), *Sporotrichum pulverulentum* (Ander et al. *Arch Microbiol* 125 (1980) 189-202), *Phlebia radiata* (Lundell et al. *Appl. Environ. Microbiol.* 56 (1990) 2623-2629), *Phanerochaete chrysosporium* (Muheim et al., *Eur. J Biochem.* 195 (1991) 369-375), *Bjerkandera* sp (De Jong et al. *Appl. Environ. Microbiol.* 60 (1994) 271-277).

U.S. Pat. No. 6,261,814 discloses use of isolated and purified enzyme system of carboxylic acid reductase from *Nocardia* sp strain, NRRL 5646 as a biocatalyst for the reduction of carboxylic acids. It requires external addition of expensive cofactors like ATP, NADPH which are difficult to regenerate in the system and hinders the isolation of the product. This process is therefore not commercially viable in terms of yield and cost.

Another U.S. Pat. No. 5,866,380 discloses a process for conversion of vanillic acid to vanillin where the white rot fungus is used and it gives only 31% yield with aldehyde. It also discloses the use of adsorbent resin in the fermentation medium.

U.S. Pat. No. 6,162,637 discloses a process for conversion of vanillic acid to vanillin using *Phanerochaete chrysosporium*, wherein 0.3 g/L substrate concentration is used for 3 days along with 0.3 g/L every day, 10% amberlite XAD resin added to finally yield 0.628 g/L vanillin.

U.S. Pat. No. 6,162,637 discloses uses of *Phanerochaete chrysosporium*, MIC 247 to reduce vanillic acid to vanillin, wherein 1.8 g/L of vanillic acid is added in doses of 0.3 g/L each day till 6 days which is a very long time for biotransformation. At the end of 6 days, 0.628 g/L of vanillin is accumulated, but only 46.5% conversion of substrate is observed which ultimately contributes to lower productivity of the overall process.

U.S. Pat. No. 6,844,019 discloses use of the organism *Micromucor isabellinus* (Zyl 849) to convert vanillic acid to vanillin, wherein vanillic acid is used for the growth of the starter culture, resulting in lower biotransformation yield. Overall 18 g of vanillic acid is added and 8.5 g of vanillin is obtained with 43.8% substrate conversion.

Hage and Schoemaker (1999) employed the basidiomycete strain *Bjerkandera* sp strain B0S55 to reduce p-anisic acid to corresponding aldehyde and alcohol. However total molar yields of aldehyde and alcohol together was 75% only (Hage et al. *Appl Microbiol Biotechnol* (1999) 52: 834-838). Other substrates studied were veratric acid, 3-chloro-4-methoxybenzoic acid, 3,5-dichloro-4-methoxy benzoic acid, 3,4-dichloro benzoic acid, 4-fluorobenzoic acid and 3-nitrobenzoic acids. All these acids were reduced, however, the fungi established equilibrium between aldehyde and alcohol production. The total molar yield of aldehyde and alcohol was 74-85%. No selectivity with respect to aldehyde and/or alcohol was obtained. And so a further separation technology is required to isolate the individual metabolites. Also the individual yields of corresponding aldehyde and alcohol is very low.

U.S. Pat. No. 7,462,470 discloses vanillin production from vanillic acid using *Pycnoporus cinnabarinus* CGMCC 1115. 80% of vanillin yield was obtained over 2 g/L of vanillic acid concentration. But the media composition used for culturing the organism contained a very high amount of nitrogen source and also a higher percentage of initial inoculum which ultimately gave the biomass cells in high concentration. So this high biocatalyst concentration converts/biotransforms a higher substrate concentration.

Biocatalytic processes for the manufacture of small, highly functionalized molecules frequently have limited productivity. A common reason for this is the presence of the reaction products that can cause inhibitory or toxic effects (making poor use of the enzyme) or promote unfavourable equilibria (giving low conversions). In each case, the product needs to be removed as soon as it is formed in order to overcome these constraints and hence increase the productivity of the biocatalytic process. ISPR techniques i.e. in-situ product removal techniques are employed where either an adsorbent resin is added in the biotransformation media to capture the product or a suitable solvent is added which extracts the product. However, when an adsorbent resin is added in the biotransformation media, separation of the resin from the biomass is difficult and further depending upon its binding capacity, the amount of resin to be added is also a limitation in cases where a large amount of resin cannot be added. The use of solvent for product capture has its own limitation of posing toxicity to the cells, thus affecting the biotransformation efficiency. Also, in both the cases, the cells once treated with solvent or added with resin cannot be reused for subsequent biotransformations and so these techniques cannot be used for continuous processes.

Microbial reduction of acids to aldehydes posses a common problem of immediate further reduction to alcohols due to aldehyde toxicity to the cells. Also high concentration of aldehyde causes great product repression in the fermentation which results in the decrease in biotransformation efficiency.

The selectivity of the process to obtain aldehyde in high concentration and yield is strongly influenced by the pH of the reaction. Most of the reductions are carried out in the pH range of 4-6.

The invention disclosed in the present invention provides a solution to the above mentioned problem of the prior art. The advantage of this invention is selectivity of aldehyde and/or alcohol at higher yields, low production cost due to cheaper media and recycling of the biomass, high final product concentration, and high productivity due to continuous system, easy downstream processing, clean process and eco friendly product.

SUMMARY OF THE INVENTION

One object of the present invention is to provide a method for biological reduction of the aryl carboxylic acids to their corresponding aldehydes and/or alcohols with high purity and high yield.

Another object of the invention is to provide a method for biological reduction of aryl carboxylic acids to their corresponding aldehydes and/or alcohols to avoid substrate inhibition effect and end product inhibition effect.

Yet another objective of present invention is to provide use of solvent for product capture without poisoning the cells resulting in increased the biotransformation efficiency.

Another object of the invention is to provide a process with alcohol at higher yields, low production cost due to cheaper media and recycling of the biomass, high final product concentration, and high productivity due to continuous system.

Another object of the present invention is to provide a process for recovery and recycling of cell culture which make the process continuous and increased in the productivity.

Yet another object of present invention is to provide a mild reaction condition, easy downstream processing, clean process and eco friendly product.

DETAILED DESCRIPTION OF THE INVENTION

Figure 1:
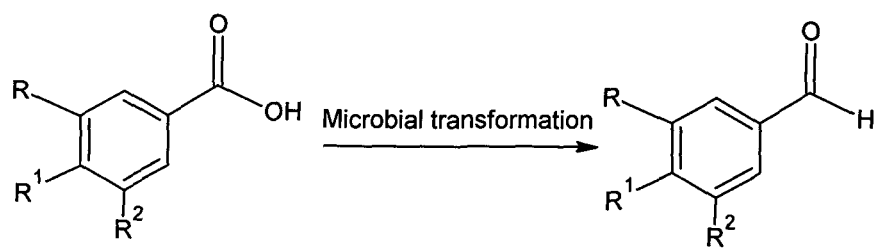
FIG. 1: shows selective reduction of Aryl Acid to Aryl Aldehyde, wherein R and/or R1 and/or R2=H, OH, NH2, alkoxy, halides, alkyl.
Figure 2:
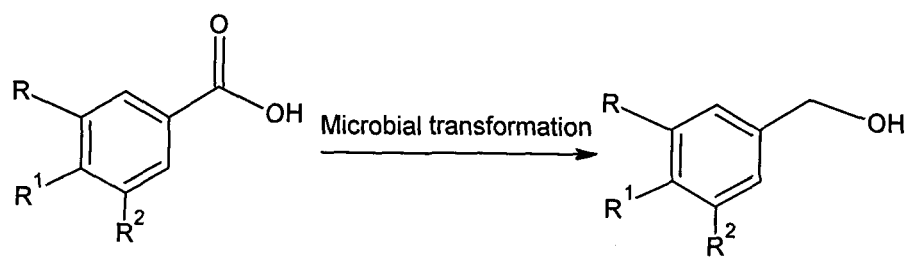
FIG. 2: shows selective reduction of Aryl Acid to Aryl Alcohol, wherein R and/or R1 and/or R2=H, OH, NH2, alkoxy, halides, and alkyl.
Figure 3:
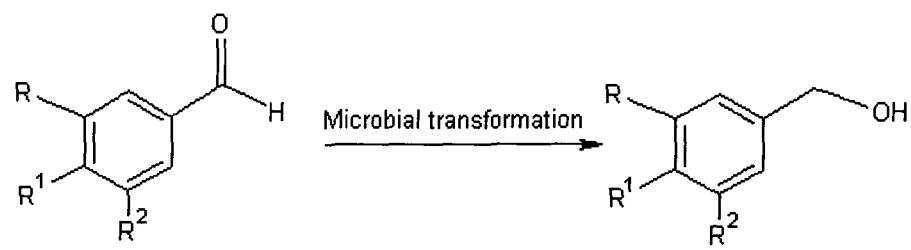
FIG. 3: shows selective reduction of Aryl Aldehyde to Aryl Alcohol, wherein R and/or R1 and/or R2=OH, NH2, OCH3, and Cl.
Figure 4:
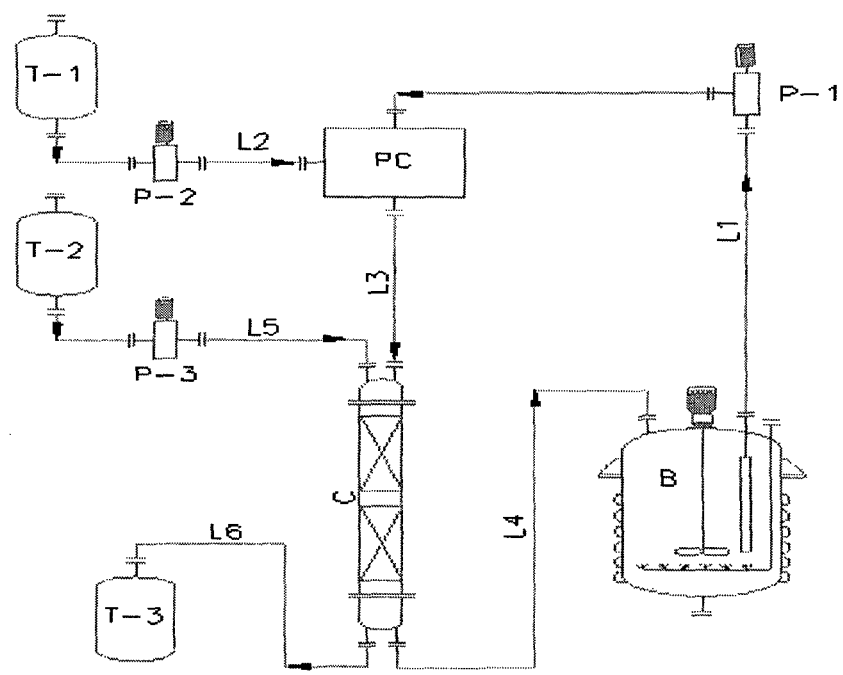
FIG. 4: shows schematic representation of the process of the invention, wherein L stands for Line of Flow; P stands for Pump; F for Membrane Filter/G1 Filter; C-capture column; B-reaction vessel; PC-pH controller.

The present invention relates to a novel method for selective reduction of aryl acids to aldehyde and/or alcohols. This reduction is specific and selective for its functional group carboxylic (—COOH), without affecting other functional group such as—R groups (—OH, —NH2, -alkyl, -alkoxy, —Br, —Cl) and their position, number on aromatic ring.

The present invention also discloses a method for selective reduction of aryl acids to aldehyde and/or alcohols by employing a white rot fungus—*Pycnoporus cinnabarinus* an organism of basidiomycete species, grown in vessel/column. The present invention also employs continuous extraction of selective product on hydrophobic adsorbent.

One of the aspects of the present invention is to provide a process for method for selective reduction of aryl acids to aldehyde and/or alcohols by employing a white rot fungus-*Pycnoporus cinnabarinus* an organism of basidiomycete species, without affecting other functional group such as—R groups (—OH, —NH2, -alkyl, -alkoxy, —Br, —Cl) and their position, number on aromatic ring. The present invention also employs continuous extraction of selective product on hydrophobic adsorbent with selective elution of aldehyde and/or alcohol with natural and/or synthetic solvent.

Another aspect of the present invention is to provide a method for biological reduction of the aryl carboxylic acids to their corresponding aldehydes and/or alcohols with high purity and high yield, wherein said process comprises: preparing the spore suspension of the culture *Pycnoporus cinnabarinus* (NCIM-1181); culturing the fungus *Pycnoporus cinnabarinus* (NCIM-1181) in a fermentor with pH 2-6 for 48-96 hrs to obtain cell pellets for biotransformation; adding aryl carboxylic acid substrate to the fermentor of above step to obtain the final concentration of 1-3 g/L for aryl carboxylic acid; wherein aryl carboxylic acid substrate is consumed for 50-90 hrs and reaction mass or fermentation broth containing aldehyde and/or alcohol product is obtained; filtering this reaction mass or fermentation broth to obtain retentate and permeate fractions, connecting capture column to the fermentor for selective extraction of an aldehyde product obtained from above said step; circulating fermentor in the capture column to extract the aldehyde selectively, wherein alcohol is captured after completion of the biotransformation; eluting the capture column to obtain the crude aldehyde and/or alcohol product in high concentration; and crystallizing the crude product to obtain pure aldehyde and/or alcohol product.

In one of the embodiment of the present invention there is provided a process for biological reduction of the aryl carboxylic acids to their corresponding aldehydes and/or alcohols with high purity and high yield, wherein the said process comprises: preparing the spore suspension of the culture *Pycnoporus cinnabarinus* (NCIM-1181); culturing the fungus *Pycnoporus cinnabarinus* (NCIM-1181) in a fermentor with pH 2-6 for 48-96 hrs to obtain cell pellets for biotransformation; adding aryl carboxylic acid substrate to the fermentor of above step to obtain the final concentration of 1-3 g/L for aryl carboxylic acid; wherein aryl carboxylic acid substrate is consumed for 50-90 hrs and reaction mass containing aldehyde and/or alcohol product is obtained; connecting capture column to the fermentor for selective extraction of an aldehyde product obtained from above said step; circulating fermentor in the capture column to extract the aldehyde selectively, wherein alcohol is captured after completion of the biotransformation; eluting the capture column to obtain crude product in high concentration; and crystallizing the crude product to obtain pure aldehyde and/or alcohol product.

In another embodiment of the present invention there is provided a process for biotransformation of aryl acids to aldehyde and/or alcohols, wherein the biotransformation may be performed in fermentor attached with pH control, dissolved oxygen, membrane system, and product extractor.

In yet another embodiment of invention there is provided a process for biotransformation of aryl carboxylic acid to aldehydes and/or alcohol, wherein aryl acid may be used for biotransformation is obtained from the group consisting of 4-hydroxy 3-methoxy benzoic acid, 3-hydroxy-4-methoxy benzoic acid, p-Hydroxy benzoic acid, gallic acid, syringic acid, anisic acid.

Another embodiment of the present invention there is provided a process for selective reduction aryl acid substrate to their aryl aldehyde and/or alcohol may not be limited to mentioned substrate and their reduction to respective aldehydes and/or of functional group, wherein R, $R_1$, $R_2$ groups (—OH, —NH2, -alkyl, -alkoxy, —Br, —Cl) at positions on the aromatic ring as shown in FIG. 1.

Another embodiment of the present invention provides a process for biotransformation of aryl carboxylic acid to aldehydes and/or alcohol, wherein aryl aldehyde may be obtained from the group consisting of 4-Hydroxy-3-methoxybenzaldehyde, 3-Hydroxy-4-ethoxybenzaldehyde, p-hydroxy benzaldehyde, 3,5-Dimethoxy-4-hydroxybenzaldehyde, 3-Amino-5-chlorobenzaldehyde.

In yet another embodiment of the present invention there is provided a process for selective reduction of aryl acid to aryl alcohol, wherein aryl alcohol may be obtained from the group consisting of 4-hydroxy-3-methoxybenzyl alcohol, p-hydroxy benzyl alcohol, 3-Amino-5-chlorobenzyl alcohol, 3-Hydroxy-4-methoxybenzyl alcohol.

According to another embodiment of the present invention, aryl carboxylic acid substrate may be added in its salt form to achieve required final concentration.

Another embodiment of the present invention, wherein biotransformation of aryl acid to their aryl aldehydes and/or alcohol may be carried out in fed batch and/or continuous manner.

According to another embodiment of the present invention, biotransformation in a fed batch may be carried out by addition of subsequent doses of substrate with concentration in the range of 1-3 g/L after complete consumption of the substrate that is added in first batch with same parameters of biotransformation.

Yet another embodiment of the present invention relates to fed batch operation of the invention wherein the biotransformation of aryl acid to aryl aldehyde and/or aryl alcohol, performed by directly feeding the substrate solution i.e. the aryl acid to the biotransformation medium and the aryl product is isolated continuously in continuous operation, while the substrate concentration is kept constant in biotransformation medium by stepwise or dropwise addition of the aryl substrate.

According to another embodiment of the present invention, the filtration may be carried out using membrane filter/G1 filter/perforated plates, having pore size at least 0.22 micron before adsorption on capture column.

According to yet another embodiment of the present invention, filtration may be done to obtain retentate comprising culture cells/spores/mycelia/pellets, and permeate comprising liquid containing aryl aldehydes and/or alcohols which is passed through the column for adsorption.

In another embodiment of the present invention, the flow rate of the circulation of the fermentation broth through the column may be adjusted in such a way that the product formed is completely adsorbed onto the column and further biotransformation of the product is paused.

In most preferred embodiment of the present invention, capture column may be packed with hydrophobic adsorbent.

In another embodiment of the present invention, the hydrophobic adsorbent used in capture column may be hydrophobic polystyrene divinyl benzene based or any polystyrene methacrylate based polymeric adsorptive resin, is selected from the group consisting of Amberlite XAD-2, Amberlite XAD-7, XAD 16, lewatit OC 1600 or OC 1064, Tulsion ADS 600, SP 700, Relite EXA 118.

In another embodiment of the present invention, the pH of capture column may be adjusted to 5-8 to favor selective binding of the product.

In most preferred embodiment of the present invention there is provided a capture column for separation of product from impurities, wherein first elution of capture column may be done with $NaHCO_3$ to remove the traces of the bound unreacted aryl carboxylic acid substrate and then with organic polar/non polar solvent depending on the solubility or miscibility of the product.

In another embodiment of the present invention, the elution of capture column may be carried out using organic polar solvent selected from the group consisting of methanol, ethanol, isopropanol, butanol, water, acetone, ethyl acetate, most preferably methanol.

According to another embodiment of the present invention, the crude product may be obtained by concentrating the elution solvent by vacuum distillation at temperature in the range of 55° C. to 65° C. and then allowing the concentrated product to cool down gradually for 6-12 hrs and/or at temperature in the range of 10-30° C.

The other embodiment of the present invention, wherein biotransformation of aryl acid to aryl aldehyde and/or alcohol may be carried out by maintaining the pH in the range of 2-6, most preferably 3-5.

In another embodiment of the present invention, the crystallization of crude product may be done in distilled water or potable water.

In yet another embodiment of the present invention, the yield and purity of aryl aldehyde and/or alcohol may be in between 84-93% and 96-99.5% respectively.

Advantages of Technology:
1) The present invention involves the use of a white rot fungus for the selective reduction of aryl acids to their corresponding aldehydes and/or alcohol at higher yields, without the formation of any byproducts or other metabolites.
2) The present invention provides recovery and recycling of cells resulting in continuously catalyze reaction in sterile medium with minimal addition of energy and/or nutrient source.
3) The present invention also provides a process with low energy consumption, low operating cost and less time requirement, recycling of substrate resulting in low production cost, which enhances productivity.
4) Thus present invention makes the process convenient and ecofriendly.

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

EXAMPLE 1

A Mycelial mass is scraped from freshly grown slant of *Pycnoporus cinnabarinus* (NCIM-1181) using glass rod and added to 10 ml of sterile water to make a spore suspension of spore count $1-4 \times 10^7$/ml. 2 L of growth media containing 2% maltose, 0.18% of diammonium tartarate, 0.05% of yeast extract, 0.05% of magnesium sulphate, 0.002% of potassium dihydrogen phosphate is formulated, pH adjusted to 5.5 and poured in 5 L fermenter/vessel/column. It is autoclaved at 121° C. for 20 minutes. After sufficient cooling, 0.1% of the spore suspension is inoculated in the growth media. Incubation was done for 72 hrs at 37° C. The dissolved oxygen concentration was set at 30% using aeration and/or agitation. After 72 hrs of growth period, small pellets of diameter around of 2-4 mm of *P. cinnabarinus* cells were obtained.

EXAMPLE 2

Reduction of 4-hydroxy-3-methoxybenzoic acid to 4-Hydroxy-3-methoxybenzaldehyde 1.5 gm 4-hydroxy-3-methoxybenzoic acid was dissolved in 10 ml of distilled water using 3 ml of 2M NaOH and added to the grown cells in fermentor of Example 1 to bring final concentration of substrate to 1.5 g/L. After addition of the substrate, pH of the broth was adjusted to 4 and dissolved oxygen concentration was set at 30%, pH was controlled at 4. The transformation was carried out at 37° C. After 5 hrs of substrate addition, circulation of broth through capture column was started with the flow rate of 19 ml/min. and the process was continued till the total substrate 4-hydroxy-3-methoxybenzoic acid gets consumed. After complete consumption of substrate column is detached from reaction vessel and subjected to washing with 100 ml of 0.1M NaHCO3 to elute traces of bound unreacted substrate. Then product 4-hydroxy-3-methoxybenzaldehyde is eluted selectively with 300 ml methanol. The eluted product is subjected to vacuum distillation at 60° C. and the residue is allowed to cool down gradually. The crude crystals of 4-hydroxy-3-methoxybenzaldehyde with 90% of purity are obtained which are separated by filtration from the mother liquor. The crude crystals are recrystallized in 15 ml of distilled water. The formed crystals are filtered through vacuum filter and washed with chilled DW to obtain white, shiny crystals of 4-Hydroxy-3-methoxybenzaldehyde with 99.5% purity and yield of 87%.

EXAMPLE 3

Reduction of p-Hydroxy Benzoic Acid to p-Hydroxy Benzaldehyde 1.5 gm of 4-hydroxy benzoic acid was dissolved in 10 ml of distilled water using 3.5 ml of 2M NaOH and added to the grown cells in fermentor of Example 1 to bring final concentration of substrate to 1.5 g/L. After addition of the substrate, pH of the broth was adjusted to 4. After 5 hrs of substrate addition, circulation of broth through capture column was started with the flow rate of 21.5 ml/min. The dissolved oxygen concentration was set at 30% and pH was controlled at 4. The transformation was carried out at 37° C. and the process was continued till the total substrate 4-hydroxy benzoic acid gets consumed. After complete consumption of substrate column is detached from reaction vessel and subjected to washing with 100 ml of 0.1M NaHCO3 to elute traces of bound unreacted substrate. Then product 4-hydroxy benzaldehyde is eluted selectively with 300 ml methanol. The eluted product is subjected to vacuum distillation at 60° C. and the residue is allowed to cool down gradually. The crude crystals of 4-hydroxy benzaldehyde with 91% of purity are obtained which are separated by filtration from the mother liquor. The crude crystals are recrystallized in 20 ml of distilled water. The formed crystals are filtered through vacuum filter and washed with chilled DW to obtain white, shiny crystals of 4-Hydroxy benzaldehyde with 98.2% purity and yield of 85%.

EXAMPLE 4

Reduction of 3-Amino-5-chlorobenzoic acid to 3-Amino-5-chlorobenzaldehyde 1.5 gm of 3-Amino-5-chlorobenzoic acid was dissolved in 10 ml of distilled water using 2 ml of 2M NaOH and added to the grown cells in fermentor of Example 1 to bring final concentration of substrate to 1.5 g/L. After addition of the substrate, pH of the broth was adjusted to 4. After 5 hrs of substrate addition, circulation of broth through capture column was started with the flow rate of 25 ml/min. The dissolved oxygen concentration was set at 30% and pH was controlled at 4. The transformation was carried out at 37° C. and the process was continued till the total substrate p-hydroxy cinnamic acid gets consumed. After complete consumption of substrate column is detached from reaction vessel and subjected to washing with 100 ml of 0.1M NaHCO3 to elute traces of bound unreacted substrate. Then product 3-Amino-5-chlorobenzaldehyde is eluted selectively with 300 ml methanol. The eluted product is subjected to vacuum distillation at 60° C. and the residue is allowed to cool down gradually. The crude crystals of p-hydroxy cinnamaldehyde with 89.5% of purity are obtained which are separated by filtration from the mother liquor. The crude crystals are recrystallized in 20 ml of distilled water. The formed crystals are filtered through vacuum filter and washed with chilled DW to obtain white crystals of 3-Amino-5-chlorobenzaldehyde with 98.5% purity and yield of 86%.

EXAMPLE 5

Reduction of 3,5 Dimethoxy-4-hydroxybenzoic acid to 3,5-Dimethoxy-4-hydroxybenzaldehyde 1.5 gm of 3,5-Dimethoxy-4-hydroxybenzoic acid was dissolved in 15 ml of distilled water using 3.2 ml of 2M NaOH and added to the grown cells in fermentor of Example 1 to bring final concentration of substrate to 1.5 g/L. After addition of the substrate, pH of the broth was adjusted to 4. After 5 hrs of substrate addition, circulation of broth through capture column was started with the flow rate of 20 ml/min. The dissolved oxygen concentration was set at 30% and pH was controlled at 4. The transformation was carried out at 37° C. and the process was continued till the total substrate 3,5-Dimethoxy-4-hydroxybenzoic acid gets consumed. After complete consumption of substrate column is detached from reaction vessel and subjected to washing with 100 ml of 0.1M NaHCO3 to elute traces of bound unreacted substrate. Then product 3,5-Dimethoxy-4-hydroxybenzaldehyde is eluted selectively with 300 ml methanol. The eluted product is subjected to vacuum distillation at 65° C. and the residue is allowed to cool down gradually. The crude crystals of 3,5-Dimethoxy-4-hydroxybenzaldehyde with 86.56% of purity are obtained which are separated by filtration from the mother liquor. The crude crystals are recrystallized in 30 ml of distilled water. The formed crystals are filtered through vacuum filter and washed with chilled DW to obtain white crystals of 3,5-Dimethoxy-4-hydroxybenzaldehyde with 96.54% purity and yield of 84.96%.

EXAMPLE 6

Reduction of 4-hydroxy-3-methoxybenzoic acid to 4-hydroxy-3-methoxybenzyl alcohol The *P. cinnabarinus* cells are grown in fermentor as per Example 1. 1.5 gm of substrate 4-hydroxy-3-methoxybenzoic acid was dissolved in 10 ml of distilled water and 3 ml of 2M NaOH and added to the grown cells of fermentor to bring the final concentration of substrate to 1.5 g/L. After substrate addition, pH is adjusted to 4 and dissolved oxygen concentration was set at 30%. The transformation was carried out at 37° C. and the process was continued till the total substrate p-hydroxy cinnamic acid gets consumed and maintained throughout the biotransformation. Reaction is continued till complete conversion of the acid substrate and the intermediate aldehyde and when the alcohol concentration has reached its highest. Then biotransformation broth rich in product, 4-hydroxy-3-methoxybenzyl alcohol is passed through the capture column packed with hydrophobic resin with controlled condition of pH with 15 ml/min of flow rate. After passing the total broth from the column almost 98% of the formed alcohol gets adsorbed on the column selectively without any other impurities. Column washed with 100 ml of 0.1M NaHCO3 to elute traces of bound unreacted substrate. Then 4-hydroxy-3-methoxybenzyl alcohol is eluted selectively with 300 ml methanol. The eluted product is subjected to vacuum distillation at 50° C. and the residue is allowed to cool down gradually. The crude crystals of 4-hydroxy-3-methoxybenzyl alcohol with 90% of purity are obtained which are separated by filtration from the mother liquor. The crude crystals are recrystallized in 25 ml of distilled water. The formed crystals are filtered through vacuum filter and washed with chilled DW to obtain white, crystals of 4-hydroxy-3-methoxybenzyl alcohol with 99% purity and yield of 92.5%.

EXAMPLE 7

Reduction of p-Hydroxy Benzoic Acid to p-Hydroxy Benzyl Alcohol

The *P. cinnabarinus* cells are grown in fermentor as per Example 1. 1.5 gm of substrate p-hydroxy benzoic acid was dissolved in 10 ml of distilled water and 3.5 ml of 2M NaOH and added to the grown cells of fermentor to bring the final concentration of substrate to 1.5 g/L. After substrate addition, pH is adjusted to 4 and dissolved oxygen concentration was set at 30%. The transformation was carried out at 37° C. and the process was continued till the total substrate p-hydroxy benzoic acid gets consumed and maintained throughout the biotransformation. Reaction is continued till complete conversion of the acid substrate and the intermediate aldehyde and when the alcohol concentration has reached its highest. Then biotransformation broth rich in product, p-hydroxy benzyl alcohol is passed through the capture column packed with hydrophobic resin with controlled condition of pH with 20 ml/min of flow rate. After passing the total broth from the column almost 95.5% of the formed alcohol gets adsorbed on the column selectively without any other impurities. Column washed with 100 ml of 0.1M NaHCO3 to elute traces of bound unreacted substrate. Then p-hydroxy benzyl alcohol is eluted selectively with 300 ml methanol. The eluted product is subjected to vacuum distillation at 50° C. and the residue is allowed to cool down gradually. The crude crystals of p-hydroxy benzyl alcohol 92.3% of purity are obtained which are separated by filtration from the mother liquor. The crude crystals are recrystallized in 30 ml of distilled water. The formed crystals are filtered through vacuum filter and washed with chilled DW to obtain white, crystals of p-hydroxy benzyl alcohol with 99% purity and yield of 92.5%.

EXAMPLE 8

Reduction of Aryl Acid to Aryl Alcohol

A) Reduction of 3-Amino-5-chlorobenzoic acid to 3-Amino-5-chlorobenzyl alcohol

The *P. cinnabarinus* cells are grown in fermentor as per Example 1. 1.5 gm of substrate 3-Amino-5-chlorobenzoic acid was dissolved in 10 ml of distilled water and 2.5 ml of 2M NaOH and added to the grown cells of fermentor to bring the final concentration of substrate to 1.5 g/L. After substrate addition, pH is adjusted to 4 and dissolved oxygen concentration was set at 30%. The transformation was carried out at 37° C. and the process was continued till the total substrate 3-Amino-5-chlorobenzoic acid gets consumed and maintained throughout the biotransformation. Reaction is continued till complete conversion of the acid substrate and the intermediate aldehyde and when the alcohol concentration has reached its highest. Then biotransformation broth rich in product, 3-Amino-5-chlorobenzyl alcohol is passed through the capture column packed with hydrophobic resin with controlled condition of pH with 25 ml/min of flow rate. After passing the total broth from the column almost 98% of the formed alcohol gets adsorbed on the column selectively without any other impurities. Column washed with 100 ml of 0.1M NaHCO3 to elute traces of bound unreacted substrate. Then p-hydroxy cinnamyl alcohol is eluted selectively with 300 ml methanol. The eluted product is subjected to vacuum distillation at 60° C. and the residue is allowed to cool down gradually. The crude crystals of p-hydroxy cinnamyl alcohol with 89.2% of purity are obtained which are separated by filtration from the mother liquor. The crude crystals are recrystallized in 30 ml of distilled water. The formed crystals are filtered through vacuum filter and washed with chilled DW to obtain white, crystals of p-hydroxy cinnamyl alcohol with 96.3% purity and yield of 88.8%.

EXAMPLE 9

B) Reduction of 4-Hydroxy-3-methoxybenzaldehyde to 4-Hydroxy-3-methoxybenzyl alcohol The *P. cinnabarinus* cells are grown in fermentor as per Example 1. 1.5 gm of substrate 4-Hydroxy-3-methoxybenzaldehyde was dissolved in 5 ml of distilled water and 2.5 ml of 2M NaOH and added to the grown cells of fermentor to bring the final concentration of substrate to 1.5 g/L. After substrate addition, pH is adjusted to 4 and dissolved oxygen concentration was set at 30%. The transformation was carried out at 37° C. and the process was continued till the total substrate 4-Hydroxy-3-methoxybenzaldehyde gets consumed and maintained throughout the biotransformation. Reaction is continued till complete conversion of the aldehyde. Then biotransformation broth rich in product, 4-Hydroxy-3-methoxybenzyl alcohol is passed through the capture column packed with hydrophobic resin with controlled condition of pH with 20 ml/min of flow rate. After passing the total broth from the column almost 98% of the formed alcohol gets adsorbed on the column selectively without any other impurities. Column washed with 100 ml of 0.1M NaHCO3 to elute traces of bound unreacted substrate. Then 4-Hydroxy-3-methoxybenzyl alcohol is eluted selectively with 300 ml methanol. The eluted product is subjected to vacuum distillation at 60° C. and the residue is allowed to cool down gradually. The crude crystals of p-hydroxy cinnamyl alcohol with 92% of purity are obtained which are separated by filtration from the mother liquor. The crude crystals are recrystallized in 20 ml of distilled water. The formed crystals are filtered through vacuum filter and washed with chilled DW to obtain white, crystals of p-hydroxy cinnamyl alcohol with 99% purity and yield of 91%.

EXAMPLE 10

Reduction of 4-Hydroxy benzaldehyde to 4-Hydroxy benzyl alcohol

The *P. cinnabarinus* cells are grown in fermentor as per Example 1. 1.5 gm of substrate 4-Hydroxy benzaldehyde was dissolved in 5 ml of distilled water and 2.5 ml of 2M NaOH and added to the grown cells of fermentor to bring the final concentration of substrate to 1.5 g/L. After substrate addition, pH is adjusted to 4 and dissolved oxygen concentration was set at 30%. The transformation was carried out at 37° C. and the process was continued till the total substrate 4-Hydroxy benzaldehyde gets consumed and maintained throughout the biotransformation. Reaction is continued till complete conversion of the aldehyde. Then biotransformation broth rich in product, 4-Hydroxy benzyl alcohol is passed through the capture column packed with hydrophobic resin with controlled condition of pH with 20 ml/min of flow rate. After passing the total broth from the column almost 95% of the formed alcohol gets adsorbed on the column selectively without any other impurities. Column washed with 100 ml of 0.1M NaHCO3 to elute traces of bound unreacted substrate. Then 4-Hydroxy benzyl alcohol is eluted selectively with 300 ml methanol. The eluted product is subjected to vacuum distillation at 60° C. and the residue is allowed to cool down gradually. The crude crystals of p-hydroxy cinnamyl alcohol with 89% of purity are obtained which are separated by filtration from the mother liquor. The crude crystals are recrystallized in 20 ml of distilled water. The formed crystals are filtered through vacuum filter and washed with chilled DW to obtain white, crystals of 4-Hydroxy benzyl alcohol with 98% purity and yield of 92.56%.

EXAMPLE 11

Reduction of 3-Hydroxy-4-methoxybenzaldehyde to 3-Hydroxy-4-methoxybenzyl alcohol The *P. cinnabarinus* cells are grown in fermentor as per Example 1. 1.5 gm of substrate 3-Hydroxy-4-methoxybenzaldehyde was dissolved in 10 ml of distilled water and 3 ml of 2M NaOH and added to the grown cells of fermentor to bring the final concentration of substrate to 1.5 g/L. After substrate addition, pH is adjusted to 4 and dissolved oxygen concentration was set at 30%. The transformation was carried out at 37° C. and the process was continued till the total substrate 3-Hydroxy-4-methoxybenzaldehyde gets consumed and maintained throughout the biotransformation. Reaction is continued till complete conversion of the aldehyde. Then biotransformation broth rich in product, 3-Hydroxy-4-methoxybenzyl alcohol is passed through the capture column packed with hydrophobic resin with controlled condition of pH with 20 ml/min of flow rate. After passing the total broth from the column almost 93% of the formed alcohol gets adsorbed on the column selectively without any other impurities. Column washed with 100 ml of 0.1M NaHCO3 to elute traces of bound unreacted substrate. Then 4-Hydroxy benzyl alcohol is eluted selectively with 300 ml methanol. The eluted product is subjected to vacuum distillation at 60° C. and the residue is allowed to cool down gradually. The crude crystals of 3-Hydroxy-4-methoxybenzyl alcohol with 91.45% of purity are obtained which are separated by filtration from the mother liquor. The crude crystals are recrystallized in 20 ml of distilled water. The formed crystals are filtered through vacuum filter and washed with chilled DW to obtain white, crystals of 3-Hydroxy-4-methoxybenzyl alcohol with 97.45% purity and yield of 93.25%.

EXAMPLE 12

Reduction of 4-hydroxy-3-methoxybenzoic acid to 4-hydroxy-3-methoxy benzaldehyde in Fed Batch Manner

*P. cinnabarinus* cells were grown in fermentor as per Example 2. The product formed is extracted using the capture column. Again a second dose of substrate 4-hydroxy-3-methoxy benzoic acid at a concentration of 1.5 g/L is added to the cells in the fermentor and reaction continued at the same conditions. The product is adsorbed on the adsorbent capture column and again fresh substrate is added in the fermentor. Reaction is continued till complete depletion of the substrate. After complete substrate depletion column detached from vessel and subjected to elution with 100 ml of 0.1M NaHCO3 to elute traces of bound unreacted substrate. Then product 4-hydroxy benzaldehyde is eluted selectively with 300 ml methanol. The eluted product is subjected to vacuum distillation at 60° C. and the residue is allowed to cool. The crude crystals of 4-hydroxy benzaldehyde with 89% of purity are obtained which are separated by filtration from the mother liquor. The crude crystals are recrystallized in 20 ml of distilled water. The formed crystals are filtered through vacuum filter and washed with chilled DW to obtain white, shiny crystals of 4-Hydroxy benzaldehyde with 99% purity and yield of 88.52%.

EXAMPLE 13

The Reduction 4-hydroxy-3-methoxybenzoic acid to 4-hydroxy-3-methoxy benzyl Alcohol in Fed Batch Manner Reduction is done using *P. cinnabarinus* cells grown in fermentor as per Example 2. The product formed is extracted using the capture column. Again a second dose of substrate 4-hydroxy-3-methoxy benzoic acid at a concentration of 1.5 g/L is added to the cells in the fermentor and reaction continued at the same conditions. Reaction is continued till complete depletion of the substrate and intermediate metabolite an aldehyde. After complete substrate consumption column connected to the reaction vessel and adsorption takes place with controlled condition of pH and 20 ml/min of flow rate. After adsorption process about 95% of formed product bound on column. After adsorption column detached from vessel and subjected to elution with 100 ml of 0.1M NaHCO$_3$ to elute traces of bound unreacted substrate. Then product 4-hydroxy-3-methoxy benzyl alcohol is eluted selectively with 300 ml methanol. The eluted product is subjected to vacuum distillation at 60° C. and the residue is allowed to cool. The crude crystals of 4-hydroxy benzaldehyde with 92% of purity are obtained which are separated by filtration from the mother liquor. The crude crystals are recrystallized in 20 ml of distilled water. The formed crystals are filtered through vacuum filter and washed with chilled DW to obtain white, crystals of 4-hydroxy-3-methoxy benzyl alcohol with 98.5% purity and yield of 92.8%.

EXAMPLE 14

Reduction of 4-Hydroxy-3-methoxybenzaldehyde to 4-Hydroxy-3-methoxybenzyl Alcohol in Fed Batch The reduction of the aryl acid 4-Hydroxy-3-methoxybenzaldehyde to 4-hydroxy-3-methoxy benzyl alcohol is done using *P. cinnabarinus* cells grown in fermentor as per Example 2. The product formed is extracted using the capture column. Again a second dose of substrate 4-Hydroxy-3-methoxybenzaldehyde at a concentration of 1.5 g/L is added to the cells in the fermentor and reaction continued at the same conditions. Reaction is continued till complete depletion of the substrate and intermediate metabolite an aldehyde. After complete substrate consumption column connected to the reaction vessel and adsorption takes place with controlled condition of pH and 20 ml/min of flow rate. After adsorption process about 97% of formed product bound on column. After adsorption column detached from vessel and subjected to elution with 100 ml of 0.1M NaHCO$_3$ to elute traces of bound unreacted substrate. Then product 4-hydroxy-3-methoxy benzyl alcohol is eluted selectively with 300 ml methanol. The eluted product is subjected to vacuum distillation at 60° C. and the residue is allowed to cool. The crude crystals of 4-Hydroxy-3-methoxybenzyl alcohol with 89% of purity are obtained which are separated by filtration from the mother liquor. The crude crystals are recrystallized in 20 ml of distilled water. The formed crystals are filtered through vacuum filter and washed with chilled DW to obtain white crystals of 4-hydroxy-3-methoxy benzyl alcohol with 97% purity and yield of 91.18%.

EXAMPLE 15

Continuous process for reduction of 4-hydroxy-3-methoxybenzoic acid to 4-hydroxy-3-methoxy benzaldehyde

*P. cinnabarinus* cells were grown in fermentor as per Example 1. 4-hydroxy-3-methoxy benzoic acid at a concentration of 1.5 g/L, glucose 0.1 g/L and Yeast extract 0.01 g/L. (Fermentor) was continuously added using pump through membrane filter to the fermentor and reaction continued as per example 2. Four adsorbent columns were attached in parallel. The product is adsorbed on the capture column. After completion of capacity of first column, adsorption process switchover to second column. The first column detached from vessel and subjected to elution with 100 ml of 0.1M NaHCO3 to elute traces of bound unreacted substrate. Then product 4-hydroxy-3-methoxy benzaldehyde is eluted selectively with 300 ml natural ethanol. The eluted product is subjected to vacuum distillation at 60° C. and the residue is allowed to cool. The crude crystals of 4-hydroxy-3-methoxybenzaldehyde with 89% of purity are obtained which are separated by filtration from the mother liquor. The crude crystals are recrystallized in 20 ml of distilled water. The formed crystals are filtered through vacuum filter and washed with chilled DW to obtain white, shiny crystals of 4-Hydroxy-3-methoxy benzaldehyde with 99% purity. Overall 19.1 gms 4-hydroxy-3-methoxy benzaldehyde was collected after 15 days.

We claim:

1. A method for biological reduction of aryl carboxylic acids to their corresponding aldehydes and/or alcohols with high purity and yield from a fermentation broth comprising:
   a) preparing a spore suspension of a culture of *Pycnoporus cinnabarinus* (NCIM-1181);
   b) culturing the *Pycnoporus cinnabarinus* (NCIM-1181) from the spore suspension in a fermentor containing culture medium at a pH range of 2-6 for 48-96 hrs to obtain cell pellets for biotransformation;
   c) adding aryl carboxylic acid substrate or derivatives thereof, to the fermentor of step (b) to obtain a final concentration of 1-3 g/L of the aryl carboxylic acid substrate, wherein the aryl carboxylic acid substrate is consumed for 50-90 hrs or adding aryl carboxylic acid continuously to maintain a concentration of aryl carboxylic acid in the fermentation broth, to obtain a fermentation broth containing an intermediate aldehyde product or a final alcohol product; and
   d) extracting the intermediate aldehyde product or final alcohol product from the fermentation broth of step (c), wherein the extracting comprises:
      i. filtering the fermentation broth 5 hrs after adding aryl carboxylic acid substrate to obtain a permeate comprising intermediate aldehyde product and a retentate, or filtering the fermentation broth from 70 hrs to 90 hrs after adding aryl carboxylic acid substrate to obtain a permeate comprising the final alcohol product and a retentate, wherein complete biotransformation occurs in 70 hrs to 90 hrs after adding the aryl carboxylic acid substrate;
      ii. passing the permeate fraction through a capture column at a pH in a range of 7-8 for selective extraction of the intermediate aldehyde product or the final alcohol product and recycling the remaining permeate and the retentate to the fermentor;
      iii. eluting the capture column with an organic solvent to obtain the intermediate aldehyde product or final alcohol product in high concentration; and
      iv. crystallizing the intermediate aldehyde product or final alcohol product from step (iii) to obtain pure aldehyde or the alcohol product.

2. The method of claim 1, wherein biotransformation is performed in the fermentor, wherein the fermentor has pH control, dissolved oxygen, a membrane system, and a product extractor.

3. The method of claim 1, wherein the carboxylic acid substrate is selected from the group comprising of 4-hydroxy 3-methoxy benzoic acid, 3-hydroxy-4-methoxy benzoic acid, p-Hydroxy benzoic acid, 3-Amino-5-chlorobenzoic acid, 3,5-Dimethoxy-4-hydroxybenzoic acid.

4. The method of claim 1, wherein the intermediate aldehyde product is obtained from the group comprising 4-Hydroxy-3-methoxybenzaldehyde, 3-Hydroxy-4-ethoxybenzaldehyde, p-hydroxy benzaldehyde, 3, 5-Dimethoxy-4-hydroxybenzaldehyde, 3-Amino-5-chlorobenzaldehyde.

5. The method of claim 1, wherein the final alcohol product is obtained from the group consisting of 4-hydroxy- 3-methoxybenzyl alcohol, p-hydroxy benzyl alcohol, 3-Amino-5-chlorobenzyl alcohol, 3-Hydroxy-4-methoxybenzyl alcohol.

6. The method of claim 1, wherein aryl carboxylic acid substrate is added in its salt form to achieve a final concentration of aryl carboxylic acid.

7. The method of claim 1, wherein biotransformation is carried out in a fed batch and/or continuous manner.

8. The method of claim 7, wherein in the fed batch mode, the aryl carboxylic acid substrate is added in batches at preselected batch volumes and batch addition frequencies over a total feed time to achieve the final concentration of the aryl carboxylic acid.

9. The method of claim 8, wherein the batch addition frequency is one batch after every 24-30 hrs.

10. The method of claim 1, wherein filtration is carried out using at least one of a membrane filter, a G1 filter, and a perforated plate, having a pore size at least 0.22 micron.

11. The method of claim 1, wherein filtration is done to obtain retentate comprising at least one of culture cells, spores, mycelia, and pellets, and liquid permeate comprising aryl aldehydes and/or alcohols which are passed through the column for adsorption.

12. The method of claim 1, wherein the capture column is packed with a hydrophobic adsorbent.

13. The method of claim 12, wherein the hydrophobic adsorbent used in the capture column is hydrophobic polystyrene divinyl benzene based or any polystyrene methacrylate based polymeric adsorptive resin.

14. The method of claim 13, wherein the adsorption resin is selected from the group consisting of Amberlite XAD-2, Amberlite XAD-7, XAD 16, lewatit OC 1600 or OC 1064, Tulsion ADS 600, SP 700, Relite EXA 118.

15. The method of claim 1, wherein the pH of the capture column is adjusted to 5-8 to favor selective binding of the aldehyde and/or alcohol product.

16. The method of claim 1, wherein a first elution is done with $NaHCO_3$ to remove traces of bound unreacted aryl carboxylic acid substrate and then with an organic polar or non-polar solvent depending on the solubility or miscibility of the product.

17. The method of claim 16, wherein the organic polar solvent is selected from the group consisting of methanol, ethanol, isopropanol, butanol, water, acetone, and ethyl acetate.

18. The method of claim 1, wherein the pH of the biotransformation is maintained at a range between 3-5.

19. The method of claim 1, further comprising in step d) iii obtaining the intermediate aldehyde product or final alcohol product by:
concentrating the elution solvent by vacuum distillation at a temperature of 60° C.; and
gradually cooling down the concentrated product for 6-12 hrs at a temperature in the range of 10-30° C.

20. The method of claim 1, wherein in step d) iv crystallization is done in distilled water or potable water.

21. The method of claim 1, wherein to yield and purity of the intermediate aldehyde product or final and/or alcohol product is in a range of 84-93% and 96-99.5% respectively.

* * * * *